US009216287B2

(12) United States Patent
You et al.

(10) Patent No.: US 9,216,287 B2
(45) Date of Patent: Dec. 22, 2015

(54) APPARATUS FOR MEASURING AND TREATING DYSPHAGIA

(75) Inventors: Heecheon You, Pohang-si (KR); Baekhee Lee, Pohang-si (KR); Kihyo Jung, Seongju-gun (KR); Giltae Yang, Goyang-si (KR); Saewon Hong, Hwaseong-si (KR); Duk Lyul Na, Seoul (KR); Youngho Lee, Hwaseong-si (KR)

(73) Assignees: POSTECH ACADEMY-INDUSTRY FOUNDATION, Pohang-Si (KR); SAMSUNG LIFE WELFARE FOUNDATION, SEOUL (KR)

( * ) Notice: Subject to any disclaimer, the term of this patent is extended or adjusted under 35 U.S.C. 154(b) by 45 days.

(21) Appl. No.: 14/235,842

(22) PCT Filed: Aug. 1, 2012

(86) PCT No.: PCT/KR2012/006132
§ 371 (c)(1),
(2), (4) Date: Jan. 29, 2014

(87) PCT Pub. No.: WO2013/019069
PCT Pub. Date: Feb. 7, 2013

(65) Prior Publication Data
US 2014/0236262 A1 Aug. 21, 2014

(30) Foreign Application Priority Data
Aug. 3, 2011 (KR) .................. 10-2011-0077503

(51) Int. Cl.
*A61N 1/00* (2006.01)
*A61N 1/36* (2006.01)
*A61B 8/08* (2006.01)
(52) U.S. Cl.
CPC ............. *A61N 1/36014* (2013.01); *A61B 8/08* (2013.01); *A61N 1/3601* (2013.01)

(58) Field of Classification Search
USPC .......................................... 607/59, 72
See application file for complete search history.

(56) References Cited

U.S. PATENT DOCUMENTS 5,891,185 A * 4/1999 Freed et al. ............... 607/72
2007/0156182 A1 7/2007 Castel

FOREIGN PATENT DOCUMENTS

| JP | 42-014380 | 8/1967 |
| JP | 58-201059 | 11/1983 |

(Continued)

OTHER PUBLICATIONS

The extended European Search Report, Feb. 23, 2015, Corresponding European Patent Application No. 12820271.0.

*Primary Examiner* — Nicole F Lavert
(74) *Attorney, Agent, or Firm* — Lex IP Meister, PLLC

(57) ABSTRACT

According to one embodiment of the present invention, an apparatus for measuring and treating dysphagia may comprise: one or more dysphagia measuring sensor units attached to the neck of a patient; one or more electrical stimulation electrode units attached to the neck of the patient to provide electrical stimulation to the neck of the patient in accordance with the dysphagia signal sensed by the dysphagia measuring sensor units so as to resolve the dysphagia; and a control unit which controls the dysphagia measuring sensor units and the electrical stimulation electrode units. Accordingly, the apparatus for measuring and treating dysphagia according to the one embodiment of the present invention has the dysphagia measuring sensor units, and the electrical stimulation electrode units which provide electrical stimulation to the neck of the patient in accordance with the dysphagia signal sensed by the dysphagia measuring sensor units so as to resolve the dysphagia, thus simultaneously enabling convenient measurement of the dysphagia and treatment of the dysphagia using the electrical stimulation electrode units.

19 Claims, 11 Drawing Sheets

(56) References Cited

FOREIGN PATENT DOCUMENTS

| | | |
|---|---|---|
| JP | 07-088112 | 4/1995 |
| JP | 11-500339 | 1/1999 |
| JP | 2001-218769 | 8/2001 |
| JP | 2006-500994 | 1/2006 |
| JP | 2007-151736 | 6/2007 |
| JP | 2008-539826 | 11/2008 |
| JP | 2010-512843 | 4/2010 |
| JP | 2011-161189 | 8/2011 |
| KR | 10-0870912 | 11/2008 |
| WO | 97/15349 | 5/1997 |
| WO | 2004/028433 | 4/2004 |

\* cited by examiner

APPARATUS FOR MEASURING AND TREATING DYSPHAGIA

TECHNICAL FIELD

The present invention relates to an apparatus for measuring and treating dysphagia. More particularly, the present invention relates to a portable apparatus for measuring and treating dysphagia.

BACKGROUND ART

Dysphagia is a term embracing difficulty occurring during the course of eating foods. Dysphagia occurs in patients having a stroke, degenerative diseases of central nerves and peripheral nerves, traumatic cerebropathy, head and neck tumors, and muscular diseases.

It is reported that dysphagia occurs in 29% to 64% of a stroke patient and in up to 81% of a Parkinson's disease patient. Further, even in the case of a disease not directly causing dysphagia, dysphagia may occur, in which a patient does not properly swallow foods due to overall perception and body states of the patient or external effects such as airway intubation or a tracheotomy. In this case, even though there is a difference in degree for each disease and cause, dysphagia may become a cause of aspiration, pneumonia, dehydration, and malnutrition and lead up to death after all.

Swallowing is constituted by an oral cavity step where foods are put into a mouth, chewed, mixed with saliva to form agglomerates, and pushed into a pharyngeal cavity, a pharyngeal cavity step where the foods flowing into the pharyngeal cavity move to an entrance of an esophagus through a series of movements by delicate coordination of various inner structures of the pharyngeal cavity, such as a sot palate excursion, a hyolaryngeal excursion, a pharyngeal peristalsis, and relaxation of an upper esophageal sphincter, and finally, an inflow step where the foods flow into the esophagus through relaxation of the upper esophagus sphincter.

Among the steps, the oral cavity step is capable of being observed by the naked eye to be relatively precisely evaluated without special equipment. However, in the case of the pharyngeal cavity step, only outwardly finely seen and experienced movement of a neck is present in swallowing, and thus a precise structure or function may be confirmed only by special inspection equipment.

Examples of a known general dysphagia measurement apparatus include a video fluoroscopic swallowing study (VFSS) apparatus and a fiberoptic endoscopic evaluation of swallowing (FEES) apparatus. In the video fluoroscopic swallowing study apparatus, a penetration image is recorded on a fluorescent screen by using an X-ray, and an anatomical structure relating to swallowing is capable of being confirmed by the naked eye. The video fluoroscopic swallowing study apparatus is used to evaluate whether functional abnormality is present while swallowing is performed. In the fiberoptic endoscopic evaluation of swallowing apparatus, a flexible endoscope is inserted through a nose to observe an inner structure of the pharyngeal cavity before and after the foods are swallowed. However, there is a drawback in that functions of the oral cavity and the pharyngeal cavity are not capable of being confirmed when swallowing is performed in practice.

The known dysphagia measurement apparatuses have several limitations in clinical use. First, the known dysphagia measurement apparatuses are large and very costly, and are not apparatuses for measuring only dysphagia, and there is difficulty in installation and use of the apparatuses without cooperation with image medical science and otolaryngology departments. Accordingly, a favorable dysphagia examination is not performed in small scale hospitals or institutions treating dysphagia. Hence, there are many cases where many dysphagia patients are ignored or dysphagia treatment is performed without precise evaluation.

Second, even though a condition of using the video fluoroscopic swallowing study apparatus or the fiberoptic endoscopic evaluation of swallowing apparatus is permitted, there is an exposure to radiation in the case of the video fluoroscopic swallowing study apparatus, and an invasive method of inserting an endoscope through a nose is used in the case of the fiberoptic endoscopic evaluation of swallowing apparatus. Accordingly, a swallowing examination should be performed within a relatively short time, and thus there is difficulty in catching of a dysphagia characteristic of each patient in everyday life.

Meanwhile, in a known dysphagia treatment method, electrical stimulation is applied to dysphagia patients having a reduction in hyoidlarynx excursion and a reduction in relaxation force of the esophagus to treat the patients. Examples of the known dysphagia treatment method include a transcutaneous electrical stimulation (TES) method and a neuromuscular electrical stimulation (NES) method.

The transcutaneous electrical stimulation method is a rehabilitation exercise treatment method in which electrical stimulation is applied to a skin of a portion damaged while a functional task is performed to stimulate nerves and muscles under the skin. In the transcutaneous electrical stimulation method, electrical stimulation is applied to a surface of a neck to induce swallowing, thereby treating dysphagia. However, the transcutaneous electrical stimulation method may be used to treat atrophied muscles or muscles having damaged nerves, but has a limit in that an actual contraction of the muscles does not occur.

In the neuromuscular electrical stimulation method, electrical stimulation is applied to the muscles having any remaining nerve distribution and functions of neurologically damaged muscles to induce muscular contraction, and the application is repeated to increase force of the muscle. The neuromuscular electrical stimulation method is applied to treat dysphagia, in which electrodes are attached to external muscles of a neck relating to swallowing to repeat swallowing and improve a muscular motion during swallowing. Chattanooga VitalSTim is manufactured as a dysphagia treatment apparatus in consideration of a precise position of the muscle to be stimulated among the external muscles of the neck relating to swallowing or a type of stimulation pattern in order to treat dysphagia by the neuromuscular electrical stimulation method.

However, in the known dysphagia treatment methods such as the transcutaneous electrical stimulation method and the neuromuscular electrical stimulation method, appropriacy or an effect of the treatment method is not capable of being monitored. Accordingly, in the case of the patients having a problem in the oral cavity step, appropriacy of treatment, a reaction of the patient, and improvement of a target function are capable of being confirmed by the naked eye. However, there is a problem in that in the case of treatment of dysphagia caused by disorder of the pharyngeal cavity step, whether treatment appropriately affects the reduced function of the pharyngeal cavity, or an effect of treatment is not capable of being immediately confirmed during treatment.

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide an apparatus for measuring and treating dysphagia simply measuring dysphagia and treating dysphagia.

Technical Solution

An exemplary embodiment of the present invention provides an apparatus for measuring and treating dysphagia including at least one dysphagia measurement sensor unit attached to a neck of a patient. At least one electrical stimulation electrode unit is attached to the neck of the patient and applies electrical stimulation to the neck of the patient according to a dysphagia signal measured in the dysphagia measurement sensor unit to resolve dysphagia. A control unit controls the dysphagia measurement sensor unit and the electrical stimulation electrode unit.

The apparatus for measuring and treating dysphagia may further include a display analysis unit connected to the control unit and displaying and analyzing the dysphagia signal.

The dysphagia measurement sensor unit may include a ultrasonic wave transmitting unit and a ultrasonic wave receiving unit.

The ultrasonic wave receiving unit may be spaced apart from the ultrasonic wave transmitting unit.

The ultrasonic wave receiving unit may surround the ultrasonic wave transmitting unit.

The ultrasonic wave transmitting unit and the ultrasonic wave receiving unit may be disposed so that a whole shape is a doughnut.

The ultrasonic wave transmitting unit and the ultrasonic wave receiving unit may be disposed so that a whole shape is a quadrangle.

The ultrasonic wave transmitting unit and the ultrasonic wave receiving unit may be disposed so that a whole shape is a polygon.

The apparatus for measuring and treating dysphagia may further include a ultrasonic wave sound absorption unit disposed between the ultrasonic wave transmitting unit and the ultrasonic wave receiving unit.

The apparatus for measuring and treating dysphagia may further include a ultrasonic wave lens attached to front surfaces of the ultrasonic wave transmitting unit and the ultrasonic wave receiving unit and covering the ultrasonic wave transmitting unit and the ultrasonic wave receiving unit.

The apparatus for measuring and treating dysphagia may further include a voice conversion device connected to the control unit and converting the dysphagia signal into a voice.

The apparatus for measuring and treating dysphagia may further include a storage device connected to the control unit and storing the dysphagia signal in real time.

The electrical stimulation electrode unit may be programmed in advance to apply electrical stimulation in real time during dysphagia.

The ultrasonic wave receiving unit may include a main ultrasonic wave receiving unit and a preliminary ultrasonic wave receiving unit adjacent to the main ultrasonic wave receiving unit.

The apparatus for measuring and treating dysphagia may further include a sensor main body in which the ultrasonic wave transmitting unit and the ultrasonic wave receiving unit are positioned.

The ultrasonic wave transmitting unit and the ultrasonic wave receiving unit may be inserted into a sensor groove formed in the sensor main body.

The sensor main body may have a curved surface.

Surfaces of the ultrasonic wave transmitting unit and the ultrasonic wave receiving unit may be connected to each other to form a curved surface.

The surfaces of the ultrasonic wave transmitting unit and the ultrasonic wave receiving unit may be exposed.

A belt groove to which a fixing belt is fixed may be formed in a rear surface of the sensor main body.

In the apparatus for measuring and treating dysphagia according to the exemplary embodiment of the present invention, it is possible to simply measure dysphagia and treat dysphagia by using an electrical stimulation electrode unit by providing the electrical stimulation electrode unit applying electrical stimulation to a neck of a patient according to a dysphagia signal measured in a dysphagia measurement sensor unit to resolve dysphagia.

Further, in the apparatus for measuring and treating dysphagia according to the exemplary embodiment of the present invention, it is possible to measure dysphagia by a simple and noninvasive method without using a complicated dysphagia measurement apparatus such as a video fluoroscopic swallowing study apparatus or a fiberoptic endoscopic evaluation of swallowing apparatus.

Further, in the apparatus for measuring and treating dysphagia according to the exemplary embodiment of the present invention, a display analysis unit displaying and analyzing the dysphagia signal is provided to treat dysphagia and at the same time, monitor a reaction of the patient, and thus it is possible to evaluate whether the patient appropriately reacts and perform a feedback role of allowing the patient to see the reaction of himself.

Further, when ultrasonic wave receiving sensitivity is weak due to disposal of a separate preliminary ultrasonic wave receiving unit, it is possible to increase ultrasonic wave receiving sensitivity.

Further, it is possible to improve a close contacting property to a human body and durability of the dysphagia measurement sensor unit by setting a surface of a sensor main body to be curved.

DESCRIPTION OF REFERENCE NUMERALS INDICATING PRIMARY ELEMENTS IN THE DRAWINGS

Figure 1:
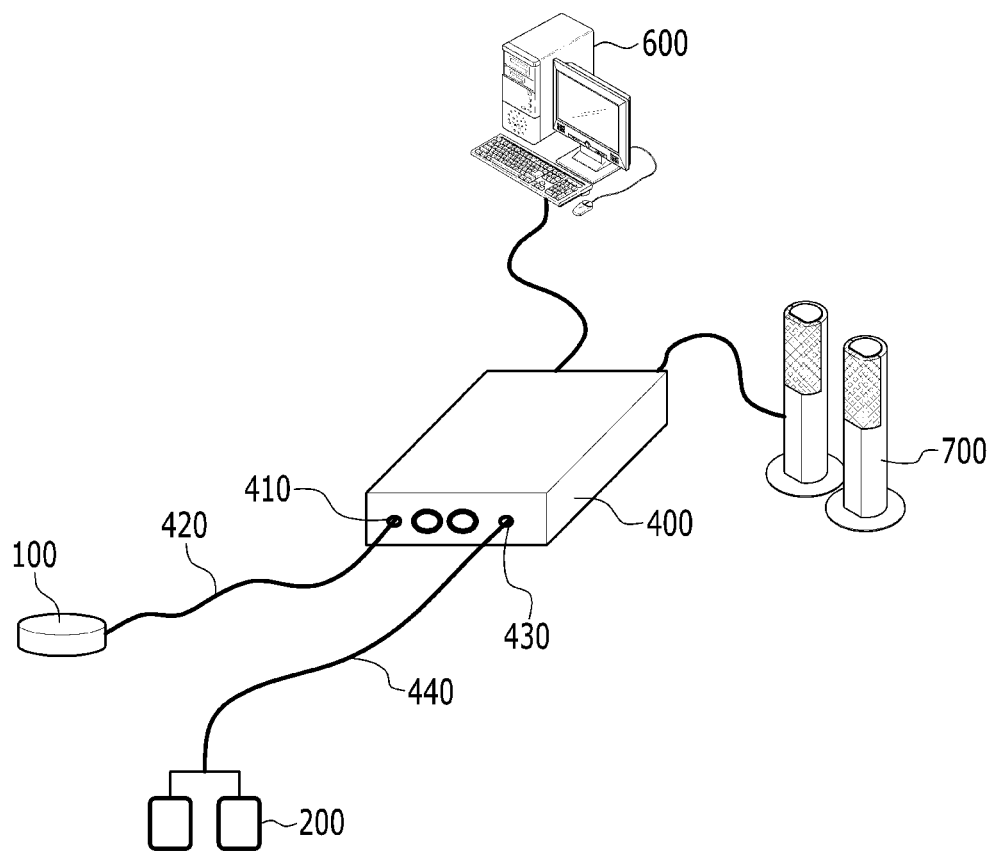
FIG. 1 is an entire schematic diagram of an apparatus for measuring and treating dysphagia according to a first exemplary embodiment of the present invention.

100: dysphagia measurement sensor unit
110: ultrasonic wave transmitting unit
120: ultrasonic wave receiving unit    130: sensor main body
140: ultrasonic wave sound absorption unit    150: ultrasonic wave lens
200: electrical stimulation electrode unit          300: control unit
400: main body                                     500: storage device
600: display analysis unit                         700: voice conversion device

MODE FOR INVENTION

Hereinafter, exemplary embodiments of the present invention will be described in detail with reference to the accompanying drawings so that those skilled in the art may easily practice the present invention. As those skilled in the art would realize, the described embodiments may be modified in various different ways, all without departing from the spirit or scope of the present invention.

In describing the present invention, parts that are not related to the description will be omitted. Like reference numerals generally designate like elements throughout the specification.

Then, an apparatus for measuring and treating dysphagia according to a first exemplary embodiment of the present invention will be described in detail with reference to FIGS. 1 to 4.

Figure 2:
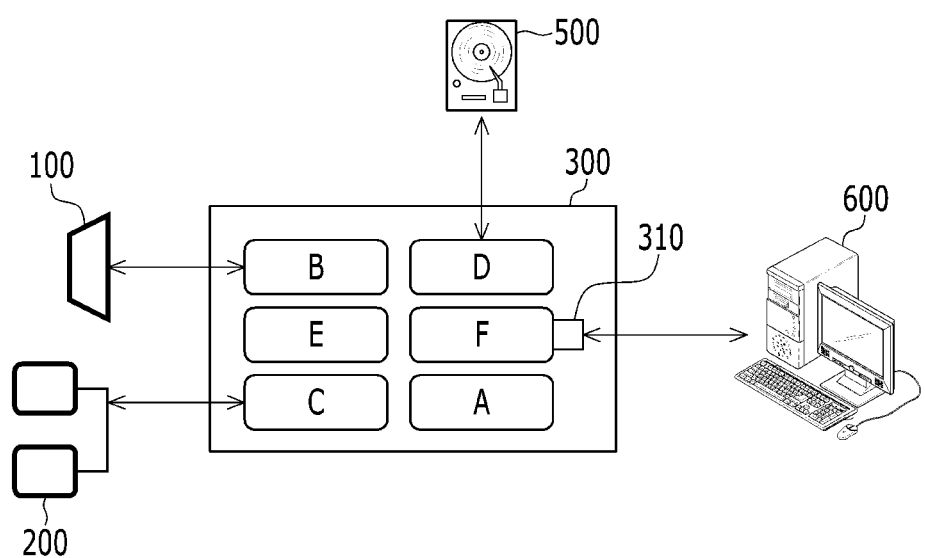
FIG. 2 is a control flowchart of a control unit of the apparatus for measuring and treating dysphagia according to the first exemplary embodiment of the present invention.
Figure 3:
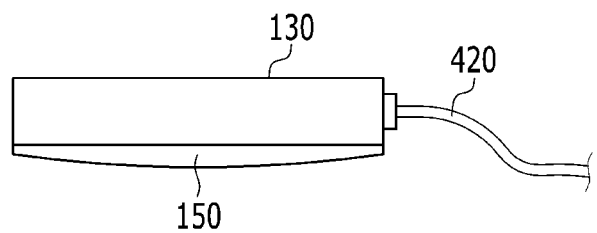
FIG. 3 is a side view of a dysphagia measurement sensor unit of the apparatus for measuring and treating dysphagia according to the first exemplary embodiment of the present invention.
Figure 4:
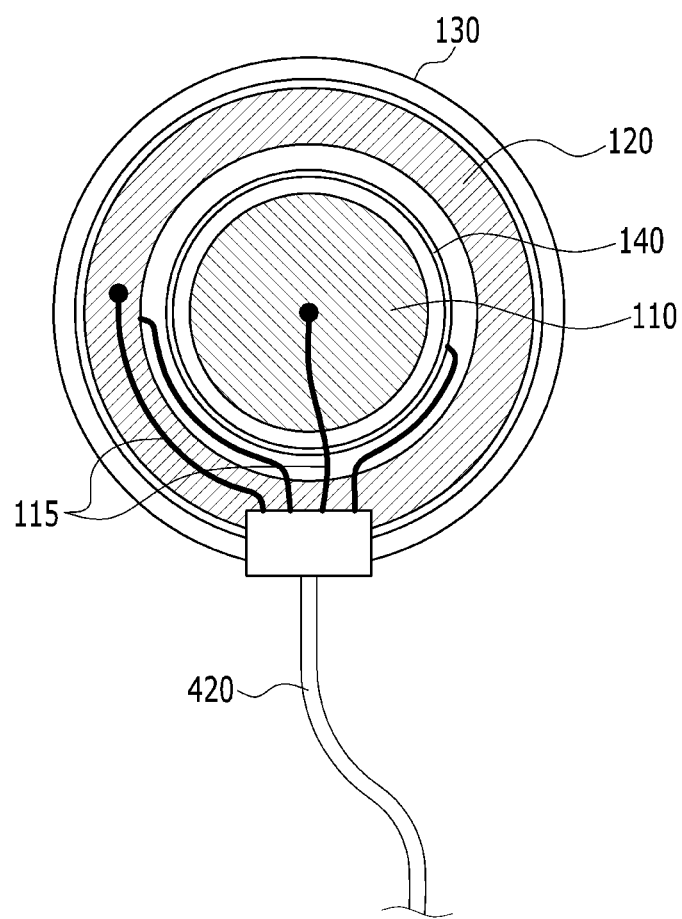
FIG. 4 is a top plan view of the dysphagia measurement sensor unit of the apparatus for measuring and treating dysphagia according to the first exemplary embodiment of the present invention.
Figure 5:
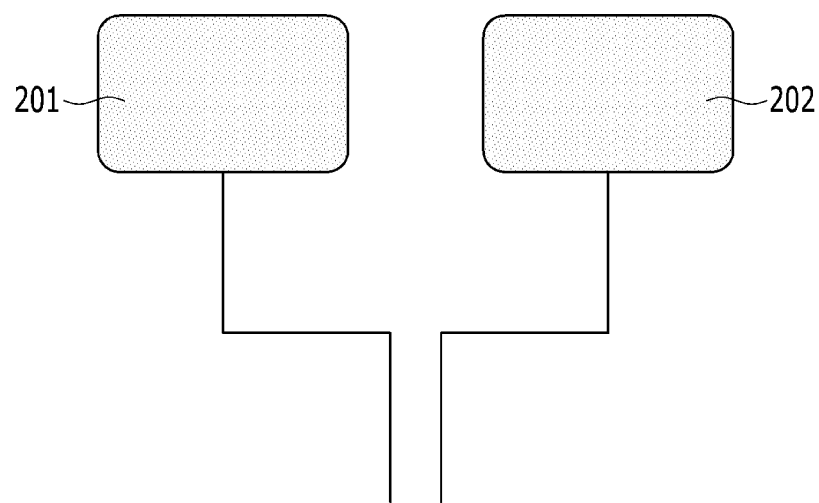
FIG. 5 is an enlarged view of an electrical stimulation electrode unit of the apparatus for measuring and treating dysphagia according to the first exemplary embodiment of the present invention.

FIG. 1 is an entire schematic diagram of the apparatus for measuring and treating dysphagia according to the first exemplary embodiment of the present invention. FIG. 2 is a control flowchart of a control unit of the apparatus for measuring and treating dysphagia according to the first exemplary embodiment of the present invention. FIG. 3 is a side view of a dysphagia measurement sensor unit of the apparatus for measuring and treating dysphagia according to the first exemplary embodiment of the present invention. FIG. 4 is a top plan view of the dysphagia measurement sensor unit of the apparatus for measuring and treating dysphagia according to the first exemplary embodiment of the present invention. FIG. 5 is an enlarged view of an electrical stimulation electrode unit of the apparatus for measuring and treating dysphagia according to the first exemplary embodiment of the present invention.

As shown in FIGS. 1 to 5, the apparatus for measuring and treating dysphagia according to the first exemplary embodiment of the present invention includes at least one dysphagia measurement sensor unit 100 attached to a neck of a patient 1, at least one electrical stimulation electrode unit 200 attached to the neck of the patient and applying electrical stimulation to the neck of the patient according to a dysphagia signal measured in the dysphagia measurement sensor unit 100 to resolve dysphagia, a control unit 300 controlling the dysphagia measurement sensor unit 100 and the electrical stimulation electrode unit 200, and a main body 400 in which the control unit 300 is positioned.

The dysphagia measurement sensor unit 100 is connected to a sensor plug 410 of the main body 400 through a sensor cable 420. The dysphagia measurement sensor unit 100 transmits a ultrasonic wave, and measures a modulation period of the ultrasonic wave modulated and reflected by foods or saliva moving to an esophagus of the patient to confirm movement of foods or saliva into the esophagus. The dysphagia measurement sensor unit 100 measures the dysphagia signal judged as abnormality of the modulation period of the ultrasonic wave. Particularly, the dysphagia measurement sensor unit 100 is a kind of ultrasonic wave sensor measuring a series of movement in a pharyngeal cavity of the neck.

As shown in FIGS. 3 and 4, the dysphagia measurement sensor unit 100 includes a ultrasonic wave transmitting unit 110 transmitting the ultrasonic wave, a ultrasonic wave receiving unit 120 detecting the ultrasonic wave reflecting and returning back, and a sensor main body 130 in which the ultrasonic wave transmitting unit 110 and the ultrasonic wave receiving unit 120 are positioned. The ultrasonic wave transmitting unit 110 and the ultrasonic wave receiving unit 120 may be positioned in one sensor main body 130 like the exemplary embodiment of the present invention. However, the ultrasonic wave transmitting unit 110 and the ultrasonic wave receiving unit 120 may be positioned in separate sensor main bodies 130.

The ultrasonic wave transmitting unit 110 is capable of having a shape of a circle, a quadrangle, or a polygon. The ultrasonic wave receiving unit 120 is spaced apart from the ultrasonic wave transmitting unit 110. The ultrasonic wave receiving unit 120 surrounds the ultrasonic wave transmitting unit 110. A connection line 115 connecting the ultrasonic wave transmitting unit 110 and the ultrasonic wave receiving unit 120 is provided to perform transmitting and receiving of a ultrasonic wave signal between the ultrasonic wave transmitting unit 110 and the ultrasonic wave receiving unit 120.

A ring-shaped ultrasonic wave sound absorption unit 140 is positioned between the ultrasonic wave transmitting unit 110 and the ultrasonic wave receiving unit 120. The ultrasonic wave sound absorption unit 140 blocks the ultrasonic wave so that the ultrasonic wave generated from the ultrasonic wave transmitting unit 110 is not directly transmitted to the ultrasonic wave receiving unit 120. The ultrasonic wave sound absorption unit 140 is formed in a molding form by using a sound absorption material between the ultrasonic wave transmitting unit 110 and the ultrasonic wave receiving unit 120. The ultrasonic wave sound absorption unit 140 may include a noise blocking material blocking a noise.

A ultrasonic wave lens 150 covering the ultrasonic wave transmitting unit 110 and the ultrasonic wave receiving unit 120 is attached on the ultrasonic wave transmitting unit 110 and the ultrasonic wave receiving unit 120. The ultrasonic wave lens 150 may improve a close contacting property to a skin, protect an inside of the sensor from impact that may be applied to the surface of the sensor, and adjust a radiation type of the ultrasonic wave by modification of a physical structure when the ultrasonic wave lens 150 comes into contact with the neck of the patient. Accordingly, the ultrasonic wave is focused on a predetermined point to increase concentrativeness of the ultrasonic wave.

As shown in FIG. 5, the electrical stimulation electrode unit 200 is connected to an electrical stimulation plug 430 of the main body 400 through an electrical stimulation cable 440. The electrical stimulation electrode units 200 are simultaneously attached to the dysphagia measurement sensor unit 100 and the neck of the patient through electrical stimulation electrodes 201 and 202. Thereby, electrical stimulation is provided to the neck of the patient according to the dysphagia signal to allow foods to flow into an esophagus through relaxation and contraction of an upper esophageal sphincter.

The control unit 300 includes a micro controller A, a ultrasonic wave sensor controller B, an electrical stimulation controller C, a data collecting device unit D, a ultrasonic wave voice conversion unit E, and an interface unit F.

The micro controller A controls the ultrasonic wave sensor controller B, the electrical stimulation controller C, the ultrasonic wave voice conversion unit E, the data collecting device unit D, and the interface unit F in the control unit 300.

The micro controller A controls the ultrasonic wave sensor controller B by a predetermined control algorithm to generate the ultrasonic wave having a predetermined frequency in the dysphagia measurement sensor unit 100.

The ultrasonic wave sensor controller B generates the continuous or pulsed ultrasonic wave in the dysphagia measurement sensor unit 100 according to the usage environment. A frequency of the generated ultrasonic wave has an oscillation period of a band of 2 to 10 MHz.

When the modulation period of the ultrasonic wave reflecting and returning back from the neck of the patient is measured in the dysphagia measurement sensor unit 100 to confirm the dysphagia signal, the micro controller A controls the electrical stimulation controller C to transmit a pattern of predetermined electrical stimulation, the intensity of a current, and an electrical stimulation period to the electrical stimulation electrode unit 200.

The electrical stimulation controller C controls to allow the electrical stimulation electrode unit 200 to apply electrical stimulation to the upper sphincter of the esophagus, such that foods flow into the esophagus and foods or saliva do not flow into an airway.

The micro controller A collects the dysphagia signal measured in the dysphagia measurement sensor unit 100 in the data collecting device unit D. The dysphagia signal collected in the data collecting device unit D is transmitted in real time to a display analysis unit 600 through a storage device 500 or the interface unit F.

The display analysis unit 600 is connected to the control unit 300. The display analysis unit 600 displays and analyzes the dysphagia signal.

The dysphagia signal measured from the dysphagia measurement sensor unit 100 may be stored by connecting the storage device 500 to the main body 400. The dysphagia signal stored in the storage device 500 may be transmitted in real time to the display analysis unit 600.

Further, a port for USB communication 310 connected to the interface unit F is situated in the main body 400. The dysphagia signal measured from the dysphagia measurement sensor unit 100 may be transmitted in real time to the display analysis unit 600 by using the port for USB communication 310 to be analyzed.

Further, the dysphagia signal measured in the dysphagia measurement sensor unit 100 may be converted into a voice frequency in the ultrasonic wave voice conversion unit E by connecting a voice conversion device 700 such as a speaker or an earphone to the main body 400. Accordingly, movement of foods in the neck may be converted into a voice to judge a precise attachment position of the dysphagia measurement sensor unit 100.

Figure 6:
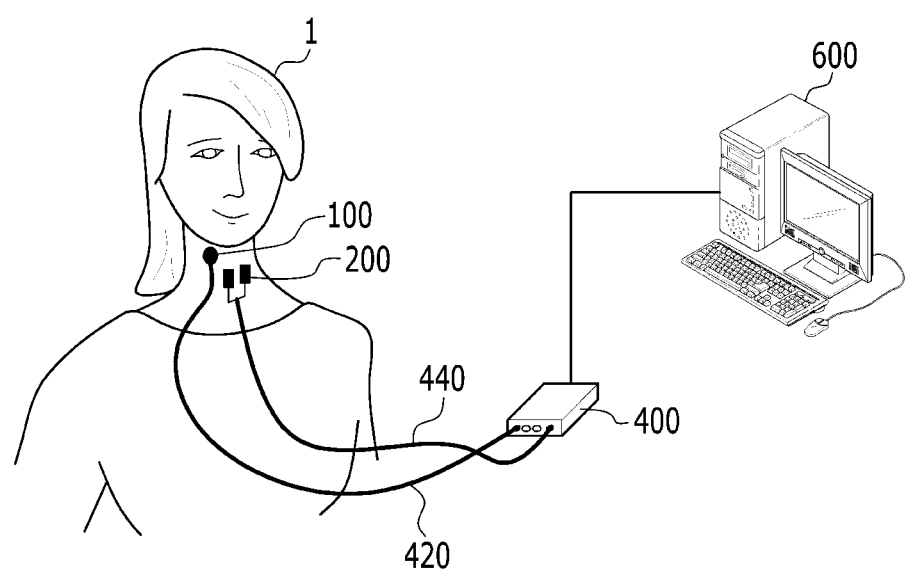
FIG. 6 is a usage illustrative view in which the apparatus for measuring and treating dysphagia according to the first exemplary embodiment of the present invention is applied to a dysphagia patient.

FIG. 6 is a usage illustrative view in which the apparatus for measuring and treating dysphagia according to the first exemplary embodiment of the present invention is applied to a dysphagia patient.

As shown in FIG. 6, the dysphagia measurement sensor unit 100 is attached to an optimum position, at which dysphagia is capable of being measured, of the neck of the patient 1. The electrical stimulation electrode unit 200 is attached to a position at which the upper sphincter of the esophagus is capable of being stimulated.

In addition, the dysphagia signal is measured by using the dysphagia measurement sensor unit 100. Dysphagia is evaluated in real time by using the display analysis unit 600. A predetermined type of electrical stimulation is applied by using the electrical stimulation electrode unit 200 according to an evaluation result to prevent foods or saliva from flowing into the airway.

Further, dysphagia of the patient may be more effectively measured by attaching the two dysphagia measurement sensor units 100 to both sides based on a front surface unit of the neck. In this case, the residual diagnosis method is the same.

Therefore, the apparatus for measuring and treating dysphagia according to the first exemplary embodiment of the present invention may simply measure dysphagia and treat dysphagia by using the electrical stimulation electrode unit 200 by providing the dysphagia measurement sensor unit 100 measuring the dysphagia signal and the electrical stimulation electrode unit 200 applying electrical stimulation to the neck of the patient according to the dysphagia signal to resolve dysphagia.

Further, the apparatus for measuring and treating dysphagia according to the exemplary embodiment of the present invention may detect and monitor a hyolaryngeal excursion and an inflow of foods into the esophagus among a series of movements of a pharyngeal cavity step relating to swallowing by providing the display analysis unit 600 displaying and analyzing the dysphagia signal, and simultaneously apply electrical stimulation to neck muscles relating to swallowing in patients having the reduced hyolaryngeal excursion and poor esophagus relaxation due to dysphagia to help a recovery of a swallowing function.

Figure 7:
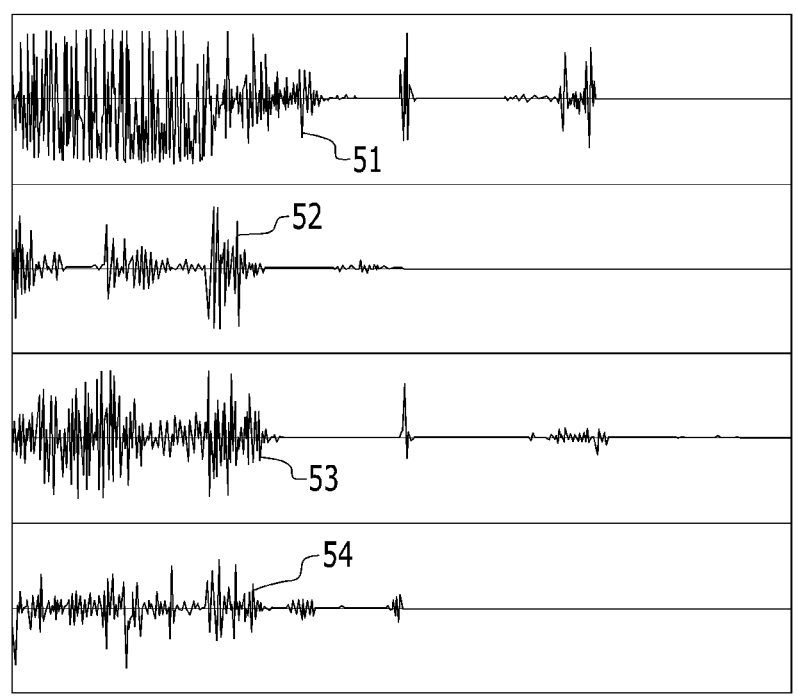
FIG. 7 is a view showing a dysphagia signal displayed on an analysis display unit of the apparatus for measuring and treating dysphagia according to the first exemplary embodiment of the present invention.

FIG. 7 is a view showing the dysphagia signal displayed on the analysis display unit of the apparatus for measuring and treating dysphagia according to the first exemplary embodiment of the present invention.

FIG. 7 shows dysphagia signals 51, 52, 53, and 54 when water, a banana, a yogurt, and biscuits are swallowed. It can be seen that various types of dysphagia signals are shown according to each food.

Meanwhile, in the first exemplary embodiment, the ultrasonic wave transmitting unit 110 has a circular, quadrangular, or polygonal shape. The ultrasonic wave receiving unit 120 is spaced apart from the ultrasonic wave transmitting unit 110 and has a structure surrounding the ultrasonic wave transmitting unit 110. However, the ultrasonic wave transmitting unit 110 and the ultrasonic wave receiving unit 120 may have a semi-doughnut shape corresponding to a half of a doughnut shape, and be disposed to face each other so that a whole shape is a doughnut.

Hereinafter, an apparatus for measuring and treating dysphagia according to a second exemplary embodiment of the present invention will be described in detail with reference to FIG. 8.

Figure 8:
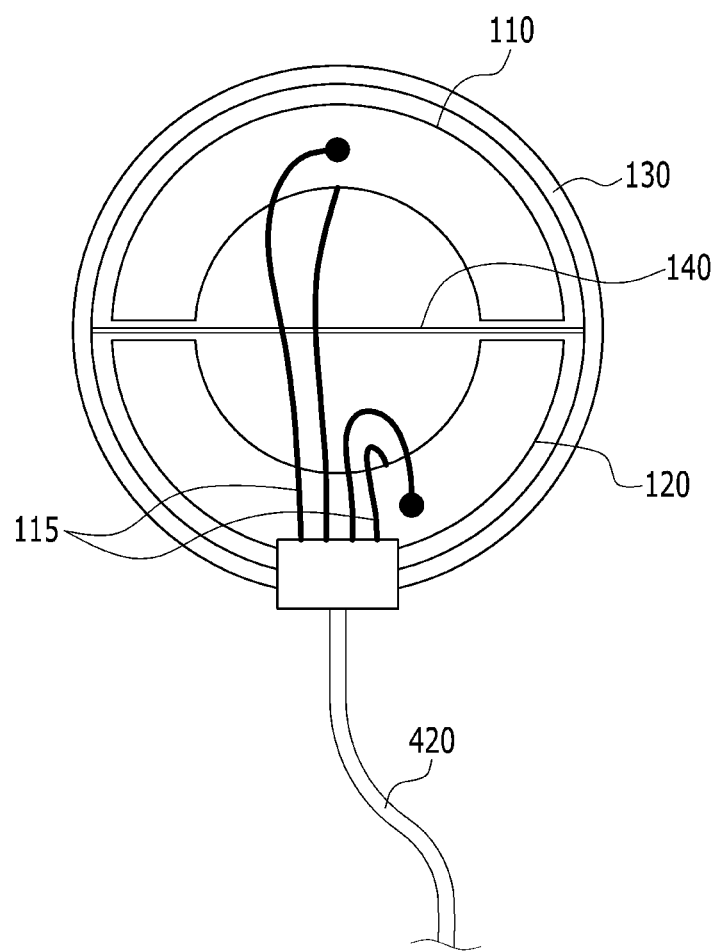
FIG. 8 is a top plan view of a dysphagia measurement sensor unit of an apparatus for measuring and treating dysphagia according to a second exemplary embodiment of the present invention.

FIG. 8 is a top plan view of a dysphagia measurement sensor unit of the apparatus for measuring and treating dysphagia according to the second exemplary embodiment of the present invention.

The second exemplary embodiment is substantially the same as the first exemplary embodiment shown in FIG. 4, with the exception of only the structures of the ultrasonic wave transmitting unit and the ultrasonic wave receiving unit. Accordingly, a repeated description thereof will be omitted.

As shown in FIG. 8, the dysphagia measurement sensor unit 100 of the apparatus for measuring and treating dysphagia according to the second exemplary embodiment of the present invention includes the ultrasonic wave transmitting unit 110 transmitting the ultrasonic wave, the ultrasonic wave receiving unit 120 detecting the ultrasonic wave reflecting and returning back, and the sensor main body 130 in which the ultrasonic wave transmitting unit 110 and the ultrasonic wave receiving unit 120 are positioned. The ultrasonic wave transmitting unit 110 and the ultrasonic wave receiving unit 120 may be positioned in one sensor main body 130 like the exemplary embodiment of the present invention. However, the ultrasonic wave transmitting unit 110 and the ultrasonic wave receiving unit 120 may be positioned in separate sensor main bodies 130.

The ultrasonic wave transmitting unit 110 has a semi-doughnut shape corresponding to a half of a doughnut shape. Even the ultrasonic wave receiving unit 120 facing the ultrasonic wave transmitting unit 110 has the semi-doughnut shape. The ultrasonic wave transmitting unit 110 and the ultrasonic wave receiving unit 120 are spaced apart from each other, and disposed so that a whole shape is a doughnut.

The connection line 115 connecting the ultrasonic wave transmitting unit 110 and the ultrasonic wave receiving unit 120 is provided to perform transmitting and receiving of a ultrasonic wave signal between the ultrasonic wave transmitting unit 110 and the ultrasonic wave receiving unit 120.

A plate-shaped ultrasonic wave sound absorption unit 140 is positioned between the ultrasonic wave transmitting unit 110 and the ultrasonic wave receiving unit 120. The ultrasonic wave sound absorption unit 140 blocks the ultrasonic wave so that the ultrasonic wave generated from the ultrasonic wave transmitting unit 110 is not directly transmitted to the ultrasonic wave receiving unit 120.

The ultrasonic wave transmitting unit 110 and the ultrasonic wave receiving unit 120 may be disposed in a plate form, or disposed at a predetermined angle based on the ultrasonic wave sound absorption unit 140. Accordingly, the ultrasonic wave may be focused on a predetermined point to increase concentrativeness of the ultrasonic wave.

Meanwhile, in the second exemplary embodiment, the ultrasonic wave transmitting unit and the ultrasonic wave receiving unit are disposed so that the whole shape is the doughnut. However, the ultrasonic wave transmitting unit and the ultrasonic wave receiving unit may be disposed in a form of quadrangles or polygons facing each other.

Hereinafter, an apparatus for measuring and treating dysphagia according to a third exemplary embodiment of the present invention will be described in detail with reference to FIGS. 9 and 10.

Figure 9:
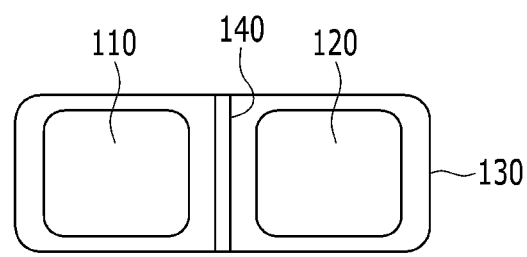
FIG. 9 is a top plan view of a dysphagia measurement sensor unit of an apparatus for measuring and treating dysphagia according to a third exemplary embodiment of the present invention.

FIG. 9 is a top plan view of a dysphagia measurement sensor unit of the apparatus for measuring and treating dysphagia according to the third exemplary embodiment of the present invention. FIG. 10 is a cross-sectional view of the dysphagia measurement sensor unit of the apparatus for measuring and treating dysphagia according to the third exemplary embodiment of the present invention.

The third exemplary embodiment is substantially the same as the second exemplary embodiment shown in FIG. 8, with the exception of only the structure of the dysphagia measurement sensor unit. Accordingly, a repeated description thereof will be omitted.

Figure 10:
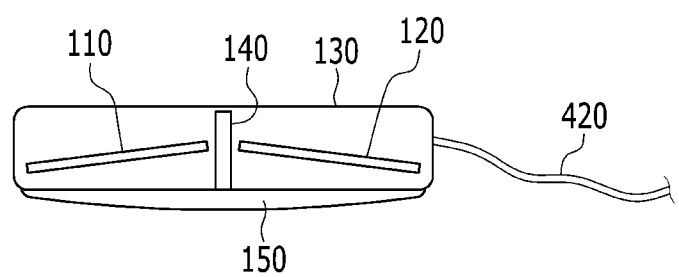
FIG. 10 is a cross-sectional view of the dysphagia measurement sensor unit of the apparatus for measuring and treating dysphagia according to the third exemplary embodiment of the present invention.

As shown in FIGS. 9 and 10, the dysphagia measurement sensor unit 100 of the apparatus for measuring and treating dysphagia according to the third exemplary embodiment of the present invention includes the ultrasonic wave transmitting unit 110 transmitting the ultrasonic wave, the ultrasonic wave receiving unit 120 detecting the ultrasonic wave reflecting and returning back, and the sensor main body 130 in which the ultrasonic wave transmitting unit 110 and the ultrasonic wave receiving unit 120 are positioned. The ultrasonic wave transmitting unit 110 and the ultrasonic wave receiving unit 120 may be positioned in one sensor main body 130 like the exemplary embodiment of the present invention. However, the ultrasonic wave transmitting unit 110 and the ultrasonic wave receiving unit 120 may be positioned in separate sensor main bodies 130.

The ultrasonic wave transmitting unit 110 has a quadrangular shape. Even the ultrasonic wave receiving unit 120 facing the ultrasonic wave transmitting unit 110 has a quadrangular shape. The ultrasonic wave transmitting unit 110 and the ultrasonic wave receiving unit 120 are spaced apart from each other. In the present exemplary embodiment, the quadrangular shape is shown. However, various types of polygons are feasible. The ultrasonic wave transmitting unit 110 and the ultrasonic wave receiving unit 120 may be disposed so that a whole shape obtaining by combining the ultrasonic wave transmitting unit 110 and the ultrasonic wave receiving unit 120 together is a quadrangle, or disposed so that the whole shape is the polygon.

The connection line 115 connecting the ultrasonic wave transmitting unit 110 and the ultrasonic wave receiving unit 120 is provided to perform transmitting and receiving of a ultrasonic wave signal between the ultrasonic wave transmitting unit 110 and the ultrasonic wave receiving unit 120.

The plate-shaped ultrasonic wave sound absorption unit 140 is positioned between the ultrasonic wave transmitting unit 110 and the ultrasonic wave receiving unit 120. The ultrasonic wave sound absorption unit 140 blocks the ultrasonic wave or an electric noise so that the ultrasonic wave or the electric noise generated from the ultrasonic wave transmitting unit 110 is not directly transmitted to the ultrasonic wave receiving unit 120.

The ultrasonic wave transmitting unit 110 and the ultrasonic wave receiving unit 120 may be disposed in a plate form, or disposed at a predetermined angle based on the ultrasonic wave sound absorption unit 140. Accordingly, the ultrasonic wave may be focused on a predetermined point to increase concentrativeness of the ultrasonic wave.

The ultrasonic wave lens 150 covering the ultrasonic wave transmitting unit 110 and the ultrasonic wave receiving unit 120 is attached on the ultrasonic wave transmitting unit 110 and the ultrasonic wave receiving unit 120. The ultrasonic wave lens 150 comes into contact with a neck of a patient, and acts to focus the ultrasonic wave on a predetermined point to increase concentrativeness of the ultrasonic wave.

Meanwhile, in the third exemplary embodiment, the ultrasonic wave transmitting unit and the ultrasonic wave receiving unit are disposed in a form of quadrangles or polygons facing each other. However, the ultrasonic wave receiving units and the ultrasonic wave transmitting unit may be disposed so that the ultrasonic wave receiving units face the ultrasonic wave transmitting unit at both sides.

Hereinafter, an apparatus for measuring and treating dysphagia according to a fourth exemplary embodiment of the present invention will be described in detail with reference to FIG. 11.

Figure 11:
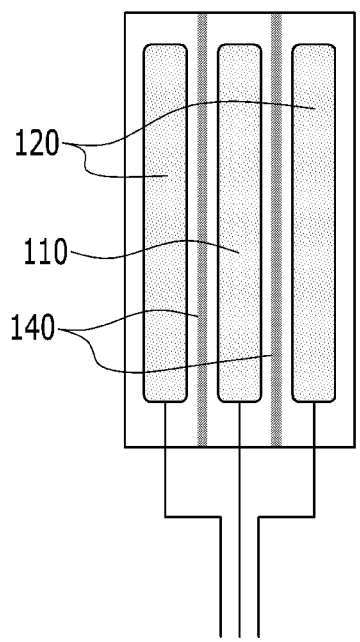
FIG. 11 is a top plan view of a dysphagia measurement sensor unit of an apparatus for measuring and treating dysphagia according to a fourth exemplary embodiment of the present invention.

FIG. 11 is a top plan view of a dysphagia measurement sensor unit of the apparatus for measuring and treating dysphagia according to the fourth exemplary embodiment of the present invention.

The fourth exemplary embodiment is substantially the same as the third exemplary embodiment shown in FIGS. 9 and 10, with the exception of only the structure of the dysphagia measurement sensor unit. Accordingly, a repeated description thereof will be omitted.

As shown in FIG. 11, the ultrasonic wave transmitting unit 110 of the dysphagia measurement sensor unit 100 of the apparatus for measuring and treating dysphagia according to the fourth exemplary embodiment of the present invention has a long rod shape. Even a pair of ultrasonic wave receiving units 120 facing each other at both sides of the ultrasonic wave transmitting unit 110 have a long rod shape. The ultrasonic wave transmitting unit 110 and the ultrasonic wave receiving units 120 are spaced apart from each other. As described above, the ultrasonic wave receiving units 120 surround the ultrasonic wave transmitting unit 110 at both sides. Accordingly, a ultrasonic wave may be more precisely received.

The plate-shaped ultrasonic wave sound absorption unit 140 is positioned between the ultrasonic wave transmitting unit 110 and one ultrasonic wave receiving unit 120. The plate-shaped ultrasonic wave sound absorption unit 140 is positioned between the ultrasonic wave transmitting unit 110 and another ultrasonic wave receiving unit 120. A pair of ultrasonic wave sound absorption units 140 block the ultrasonic wave so that the ultrasonic wave generated from the ultrasonic wave transmitting unit 110 is not directly transmitted to the ultrasonic wave receiving unit 120.

Meanwhile, in the fourth exemplary embodiment, the ultrasonic wave receiving unit and the ultrasonic wave transmitting unit are disposed so that one ultrasonic wave receiving unit faces the ultrasonic wave transmitting unit and another ultrasonic wave receiving unit faces the ultrasonic wave transmitting unit. However, a fifth exemplary embodiment where a separate preliminary ultrasonic wave receiving unit is disposed is feasible.

Hereinafter, an apparatus for measuring and treating dysphagia according to the fifth exemplary embodiment of the present invention will be described in detail with reference to FIGS. 12 and 13.

Figure 12:
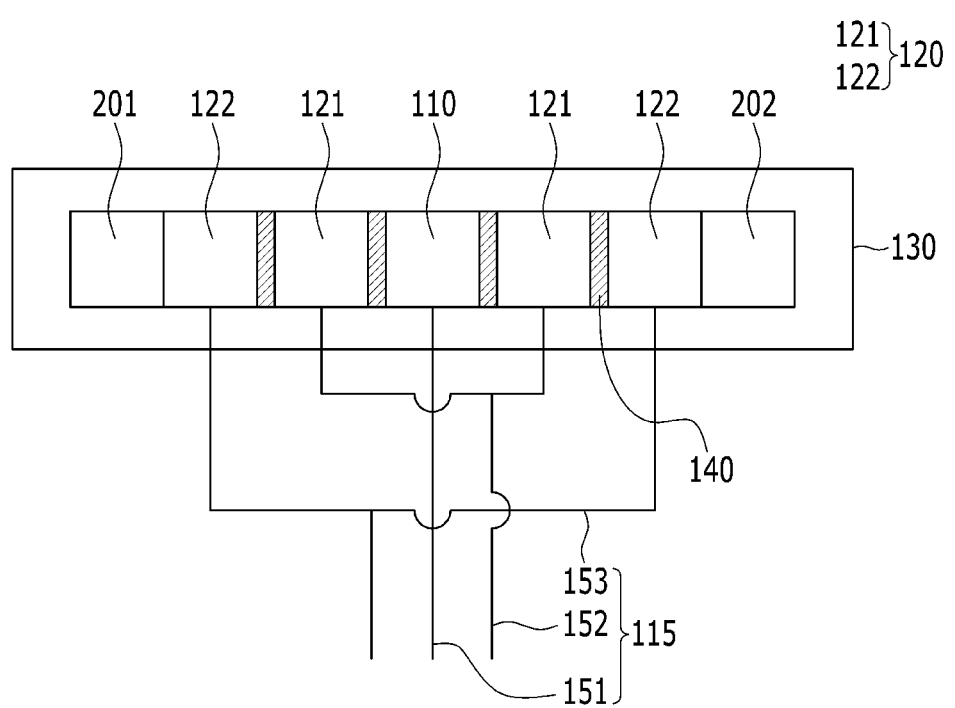
FIG. 12 is a top plan view of a dysphagia measurement sensor unit of an apparatus for measuring and treating dysphagia according to a fifth exemplary embodiment of the present invention.

FIG. 12 is a top plan view of a dysphagia measurement sensor unit of the apparatus for measuring and treating dysphagia according to the fifth exemplary embodiment of the present invention. FIG. 13 is a perspective view of the dysphagia measurement sensor unit of the apparatus for measuring and treating dysphagia according to the fifth exemplary embodiment of the present invention.

The fifth exemplary embodiment is substantially the same as the fourth exemplary embodiment shown in FIG. 11, with the exception of only the structure of the dysphagia measurement sensor unit. Accordingly, a repeated description thereof will be omitted.

Figure 13:
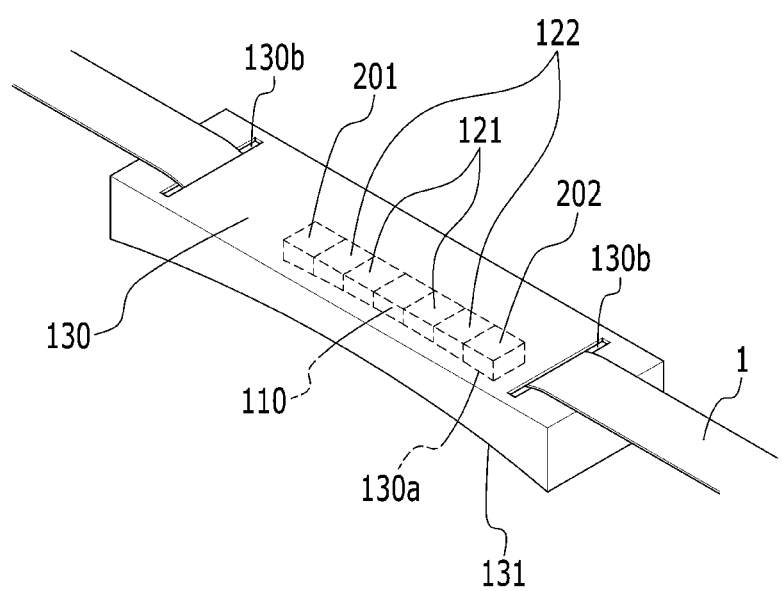
FIG. 13 is a perspective view of the dysphagia measurement sensor unit of the apparatus for measuring and treating dysphagia according to the fifth exemplary embodiment of the present invention.

As shown in FIGS. 12 and 13, the dysphagia measurement sensor unit 100 of the apparatus for measuring and treating dysphagia according to the fifth exemplary embodiment of the present invention includes the ultrasonic wave transmitting unit 110 having a quadrangle shape, a pair of ultrasonic wave receiving units 120 facing each other at both sides of the ultrasonic wave transmitting unit 110, and the sensor main body 130 in which the ultrasonic wave transmitting unit 110 and the ultrasonic wave receiving units 120 are positioned. The ultrasonic wave receiving units 120 are arranged at regular intervals at both sides of the ultrasonic wave transmitting unit 110 while the ultrasonic wave transmitting unit 110 is interposed between the ultrasonic wave receiving units 120. The ultrasonic wave receiving units 120 include a main ultrasonic wave receiving unit 121 and a preliminary ultrasonic wave receiving unit 122 that is adjacent to the main ultrasonic wave receiving unit 121. In the case where ultrasonic wave receiving sensitivity is weak, the preliminary ultrasonic wave receiving unit 122 is operated together with the main ultrasonic wave receiving unit 121 to increase ultrasonic wave receiving sensitivity.

The plate-shaped ultrasonic wave sound absorption unit 140 is positioned between the ultrasonic wave transmitting unit 110 and one main ultrasonic wave receiving unit 121. The plate-shaped ultrasonic wave sound absorption unit 140 is positioned between the ultrasonic wave transmitting unit 110 and another main ultrasonic wave receiving unit 121. A pair of ultrasonic wave sound absorption units 140 block the ultrasonic wave so that the ultrasonic wave generated from the ultrasonic wave transmitting unit 110 is not directly transmitted to the main ultrasonic wave receiving unit 121.

The connection line 115 connecting the ultrasonic wave transmitting unit 110 and the ultrasonic wave receiving unit 120 to transmit and receive a ultrasonic wave signal includes a transmitting connection line 151 transmitting the ultrasonic wave signal of the ultrasonic wave transmitting unit 110, a first receiving connection line 152 connecting the ultrasonic wave signal between a pair of main ultrasonic wave receiving units 121, and a second receiving connection line 153 connecting the ultrasonic wave signal between a pair of preliminary ultrasonic wave receiving units 122.

As described above, the ultrasonic wave receiving unit 120 includes the preliminary ultrasonic wave receiving unit 122. Accordingly, a receiving range thereof is widened, and thus ultrasonic wave receiving performance becomes excellent.

A surface 131 of the sensor main body 130 is a curved surface with the center being sunken. A sensor groove 130a is formed in the sensor main body 130. The ultrasonic wave transmitting unit 110 and the ultrasonic wave receiving unit 120 are inserted into the sensor groove 130a. Accordingly, surfaces of the ultrasonic wave transmitting unit 110 and the ultrasonic wave receiving unit 120 are connected to each other to form the curved surface.

Accordingly, the degree of contact of the dysphagia measurement sensor unit 100 may be favorably maintained regardless of curvature of a human body. Therefore, a close contacting property of the dysphagia measurement sensor unit 100 to the human body may be improved, and durability of the dysphagia measurement sensor unit 100 may be improved.

In this case, the surfaces of the ultrasonic wave transmitting unit 110 and the ultrasonic wave receiving unit 120 are exposed. Lateral surface units and rear surface units of the ultrasonic wave transmitting unit 110 and the ultrasonic wave receiving unit 120 are not exposed to the outside. When the lateral surface units and the rear surface units of the ultrasonic wave transmitting unit 110 and the ultrasonic wave receiving unit 120 are exposed to the outside, a noise problem may occur, and a serious problem may occur in terms of durability of the sensor of the dysphagia measurement sensor unit 100.

Further, the electrical stimulation electrodes 201 and 202 may be provided in the dysphagia measurement sensor unit 100. That is, the electrical stimulation electrodes 201 and 202 may be arranged on an external side of the ultrasonic wave receiving unit 120. Accordingly, dysphagia may be measured and treated simultaneously by only one dysphagia measurement sensor unit 100.

Further, a plurality of belt grooves 130b are formed on a rear surface of the sensor main body 130. A fixing belt 1 may be inserted into the belt grooves 130b to easily fix the dysphagia measurement sensor unit 100 to a neck portion of a human body. Accordingly, a stable and precise sensing operation is feasible.

While this invention has been described in connection with what is presently considered to be practical exemplary embodiments, it is to be easily understood by those skilled in the art that the invention is not limited to the disclosed embodiments, but, on the contrary, is intended to cover various modifications and equivalent arrangements included within the spirit and scope of the appended claims.

The invention claimed is:

1. An apparatus for measuring and treating dysphagia comprising:
   at least one dysphagia measurement sensor unit attached to a neck of a patient,
   at least one electrical stimulation electrode unit attached to the neck of the patient and applying electrical stimulation to the neck of the patient according to a dysphagia signal measured in the dysphagia measurement sensor unit to resolve dysphagia, and
   a control unit controlling the dysphagia measurement sensor unit and the electrical stimulation electrode unit,
   wherein the dysphagia measurement sensor unit includes a ultrasonic wave transmitting unit and a ultrasonic wave receiving unit.

2. The apparatus for measuring and treating dysphagia of claim 1, further comprising:
   a display analysis unit connected to the control unit and displaying and analyzing the dysphagia signal.

3. The apparatus for measuring and treating dysphagia of claim 1, wherein the ultrasonic wave receiving unit is spaced apart from the ultrasonic wave transmitting unit.

4. The apparatus for measuring and treating dysphagia of claim 1, wherein the ultrasonic wave receiving unit surrounds the ultrasonic wave transmitting unit.

5. The apparatus for measuring and treating dysphagia of claim 1, wherein the ultrasonic wave transmitting unit and the ultrasonic wave receiving unit are disposed so that a whole shape is a doughnut.

6. The apparatus for measuring and treating dysphagia of claim 1, wherein the ultrasonic wave transmitting unit and the ultrasonic wave receiving unit are disposed so that a shape is a quadrangle.

7. The apparatus for measuring and treating dysphagia of claim 1, wherein the ultrasonic wave transmitting unit and the ultrasonic wave receiving unit are disposed so that a shape is a polygon.

8. The apparatus for measuring and treating dysphagia of claim 1, further comprising: a ultrasonic wave sound absorption unit disposed between the ultrasonic wave transmitting unit and the ultrasonic wave receiving unit.

9. The apparatus for measuring and treating dysphagia of claim 1, further comprising: a ultrasonic wave lens attached to front surfaces of the ultrasonic wave transmitting unit and the ultrasonic wave receiving unit and covering the ultrasonic wave transmitting unit and the ultrasonic wave receiving unit.

10. The apparatus for measuring and treating dysphagia of claim 1, further comprising:
    a voice conversion device connected to the control unit and converting the dysphagia signal into a voice.

11. The apparatus for measuring and treating dysphagia of claim 1, further comprising:
    a storage device connected to the control unit and storing the dysphagia signal in real time.

12. The apparatus for measuring and treating dysphagia of claim 1, wherein the electrical stimulation electrode unit is programmed in advance to apply the electrical stimulation in real time during the dysphagia.

13. The apparatus for measuring and treating dysphagia of claim 3, wherein the ultrasonic wave receiving unit includes a main ultrasonic wave receiving unit and a preliminary ultrasonic wave receiving unit adjacent to the main ultrasonic wave receiving unit.

14. The apparatus for measuring and treating dysphagia of claim 13, further comprising:
    a sensor main body in which a ultrasonic wave transmitting unit and the ultrasonic wave receiving unit are positioned.

15. The apparatus for measuring and treating dysphagia of claim 14, wherein the ultrasonic wave transmitting unit and the ultrasonic wave receiving unit are inserted into a sensor groove formed in the sensor main body.

16. The apparatus for measuring and treating dysphagia of claim 15, wherein the sensor main body has a curved surface.

17. The apparatus for measuring and treating dysphagia of claim 16, wherein surfaces of a ultrasonic wave transmitting unit and a ultrasonic wave receiving unit are connected to each other to form a curved surface.

18. The apparatus for measuring and treating dysphagia of claim 17, wherein the surfaces of the ultrasonic wave transmitting unit and the ultrasonic wave receiving unit are exposed.

19. The apparatus for measuring and treating dysphagia of claim 18, wherein a belt groove to which a fixing belt is fixed is formed in a rear surface of a sensor main body.

\* \* \* \* \*